(12) United States Patent
Eliav

(10) Patent No.: US 6,813,793 B2
(45) Date of Patent: Nov. 9, 2004

(54) TOOTHBRUSH WITH LINEAR AND ROTARY FIELDS

(75) Inventor: Eyal Eliav, New York, NY (US)

(73) Assignee: Colgate-Palmolive Company, New York, NY (US)

(*) Notice: Subject to any disclaimer, the term of this patent is extended or adjusted under 35 U.S.C. 154(b) by 0 days.

(21) Appl. No.: 10/260,078

(22) Filed: Sep. 27, 2002

(65) Prior Publication Data

US 2004/0060133 A1 Apr. 1, 2004

(51) Int. Cl.[7] .......................... A46B 13/00; A47L 21/02
(52) U.S. Cl. ........................... 15/22.2; 15/22.1; 15/28
(58) Field of Search .................. 15/22.1, 22.2, 15/22.4, 28

(56) References Cited

U.S. PATENT DOCUMENTS

| | | | |
|---|---|---|---|
| 4,633,542 A | * | 1/1987 | Taravel .................. 15/167.1 |
| 5,353,460 A | * | 10/1994 | Bauman .................. 15/22.1 |
| 5,617,603 A | * | 4/1997 | Mei ........................ 15/22.1 |
| 6,463,615 B1 | * | 10/2002 | Gruber et al. ............ 15/22.1 |
| 2003/0066145 A1 | * | 4/2003 | Prineppl .................. 15/22.1 |
| 2003/0140435 A1 | * | 7/2003 | Eliav et al. ............... 15/22.1 |
| 2003/0140437 A1 | * | 7/2003 | Eliav et al. ............... 15/22.2 |

* cited by examiner

*Primary Examiner*—Terrence R. Till
*Assistant Examiner*—Laura C Cole
(74) *Attorney, Agent, or Firm*—Harris Wolin; Henry S. Goldfine; Matthew K. Ryan

(57) ABSTRACT

A powered toothbrush to provide oral hygiene having a brush section with a first bristle carrier that is powered and driven to rotate in a first path of motion. A second bristle field including a plurality of brush elements extends from a base support of the brush section. An extension member having an end attached to the first bristle carrier and extending outwardly therefrom and at least partially into the second bristle field is also provided on the brush section whereby the extension moves upon movement of the first bristle carrier in the first path of motion to move the second bristle field in a second path of motion. The bristle fields may include a variety of elastomeric and/or non-elastomeric bristles to provide cleaning, polishing, whitening and stimulation to the teeth and gums.

28 Claims, 7 Drawing Sheets

TOOTHBRUSH WITH LINEAR AND ROTARY FIELDS

BACKGROUND OF THE INVENTION

1. Field of the Invention

The present invention relates to powered oral care products, and more specifically, powered toothbrushes that have distinct head sections.

2. Discussion of Related Art

Toothbrushes provide many oral hygiene benefits. For example, toothbrushes remove plaque and food debris to help avoid tooth decay and disease. They remove stained pellicle from the surface of each tooth to help whiten the teeth. Also, the bristles combined with the brushing motion will massage the gingival tissue for stimulation and increased health of the tissue.

Powered toothbrushes have been available for some time. Powered toothbrushes have advantages over manual (non-powered) toothbrushes in that they impart movement to the bristles at much higher speeds than possible manually. They also may impart different types and directions of motion. These motions, generally in combination with manual movement of the toothbrush by the user, provide superior cleaning than manual toothbrushes. Typically, powered toothbrushes are powered by disposable or rechargeable batteries that power an electric motor that in turn drives the toothbrush head.

Known powered toothbrushes include a brush head with a bristle carrier portion that rotates, oscillates or vibrates in some manner so as to clean the teeth. The bristles, which typically comprise bristle tufts, are generally uniform with one end fixed into the bristle carrier portion and the other end free to contact the surface of the teeth while brushing. The free ends of the various tufts present a surface envelope that is capable of some deformation when the bristles bend. When in contact with the surface to be brushed, the bristles may deform so that the surface envelope tends to conform to the complex surface of the teeth. Human teeth generally lie in a "C" shaped curve within the upper and lower jaws, and each row of teeth consequently have a convex outer curve and concave inner curve. Individual teeth often have extremely complex surfaces, with areas that may be flat, concave, or convex. The more precise conformation between the bristles and the tooth surface, the more effective the toothbrush may be in cleaning, whitening and stimulating.

Known powered toothbrushes typically arrange the bristles in a compact conical or cylindrical pattern on a generally circular, disk-shaped bristle carrier. The powered toothbrush heads are traditionally compact, generally oval in shape and the heads are produced with a flat trimmed bristle pattern. Alternatively, other head shapes and bristle patterns are available.

One example of a powered toothbrush is depicted in U.S. Pat. No. 5,625,916 to McDougall, which is hereby incorporated by reference in its entirety. The toothbrush shown in McDougall has a disc-shaped bristle carrier. The bristle carrier, and thus the bristles, are driven in a vibrating or oscillating manner, which may be illustrated by FIGS. 1A–1C. A toothbrush 5 comprises a handle portion 10 at a proximal end of the toothbrush 5 and a head 11 at a distal end of the toothbrush 5. The handle portion 10 has compartments for containing a powered motor 14 and batteries 15 and 16. The head 11 includes a generally circular bristle holder 13.

A rotatable shaft 12 extends from the motor 14 to the head 11. A shaft coupling 17 may be located along the shaft 12 and configured to provide for the shaft 12 to be separated at a point between the motor 14 and the head 11. This permits the shaft to be removed from the toothbrush 5, e.g., for cleaning or replacement.

The head 11 includes a post 18 that provides a rotational pivot axis for the bristle holder 13 containing bristles 19. The distal end of the shaft 12 has a journal or offset 20 that is radially displaced from the longitudinal axis of the shaft 12, which may be integrally formed therewith. The bristle holder 13 has a slot 22 that receives the offset 20. The offset 20 and slot 22 are configured so as to be oriented toward the intersection of the shaft 12 axis and the longitudinal axis of the post 18. When the motor 14 rotates the shaft 12, the motion of the offset 20 defines a circle about the shaft 12 axis and drivingly engages the slot 22 such that the bristle holder 13 vibrates or oscillates about the post 18 axis through a rotational angle A. The rotational angle A is defined by the displacement of the offset 20 from the shaft 12 axis relative to the diameter of the bristle holder 13.

Although powered toothbrushes such as described immediately above provide advantages over manual toothbrushes, they are subject to various limitations. Providing a rotating or oscillating bristle holder with a typical oblong or oval toothbrush head constrains the size of the moving bristle holder, and consequently the area of bristles available for teeth cleaning. Also, when the bristles are placed in contact with the teeth during brushing, there is less bristle contact with adjacent areas, such as the gums. Thus, while these compact bristle patterns provide for cleaning, there is minimal whitening and stimulation.

One attempt to overcome the limitations of a small powered bristle area is shown in the toothbrush of U.S. Pat. No. 6,000,083 to Blaustein et al. The toothbrush in Blaustein et al. has a bristle area and pattern similar to a manual toothbrush, but an area of the bristles has simply been replaced by a powered bristle section. The result is that the head has a powered or moving bristle section and static bristle section. The limitation of the toothbrush of Blaustein et al. is that the static bristle section provides no better cleaning, whitening or stimulation than a manual toothbrush.

International Application No. PCT/EP01/07615 to Braun GmbH discloses a powered toothbrush with two separate bristle sections that can move. Each bristle part may have a different range and type of motion. However, only one bristle part is powered. The other unpowered bristle part moves due to a resonance effect imparted by the frequency of the movement of the first bristle part.

This free resonance causes a number of difficulties. First, because any contact between the bristle parts will dampen or cancel any resonance of the unpowered bristle part, the unpowered bristle part "floats" separately from the powered bristle part.

This necessitates separation or gaps between them. These gaps expose the internal workings of the head to foreign matter such as water, saliva, toothpaste, and food particles. This foreign matter may interfere with the workings of the unpowered bristle head. For example, the unpowered bristle part is spring-loaded to assist its resonance. Foreign matter may accumulate on or around the spring, interfering with its function. In addition, food particles may remain in the head and may fester and host microorganisms, which are undesirable if not potentially harmful when introduced directly into the mouth.

Another limitation of such a design is that movement of the unpowered bristle part may be dampened by contact with the teeth, or lessened when the frequency of the powered part shifts from the resonance frequency. This can occur due to pressure imparted against the powered bristle part by the teeth or gums during brushing. Finally, the energy imparted to the unpowered bristle part is only a portion of the energy input into the powered part. Therefore, the unpowered bristle part is less effective in cleaning than the powered part, limiting the overall effectiveness of the toothbrush.

Thus, there is a need in the art for a powered toothbrush with increased effectiveness through a larger area of powered or driven bristles than known powered toothbrushes. There is also a need for a toothbrush having increased whitening and stimulation than known toothbrushes. There is further a need for such improved toothbrushes to be comparable in manufacturing and purchasing costs as known powered toothbrushes.

OBJECTS OF THE INVENTION

It is therefore a general object of the present invention to provide a powered toothbrush which avoids the aforementioned deficiencies of the known related art.

It is also an object of the present invention to provide a powered toothbrush which provides a more precise conformation between the bristles and the tooth surface.

It is further an object of the present invention to provide a powered toothbrush which results in increased cleaning, whitening and stimulation of the teeth and gums than known toothbrushes.

It is still a further object of the present invention to provide a powered toothbrush which achieves increased effectiveness by means of a larger area of powered or driven bristles than known powered toothbrushes.

It is yet another object of the present invention to provide a powered toothbrush which is comparable in manufacturing and purchasing costs as known powered toothbrushes.

Various other objects, advantages and features of the present invention will become readily apparent from the ensuing detailed description and the novel features will be particularly pointed out in the appended claims.

SUMMARY OF THE INVENTION

The present invention relates to a powered toothbrush having at least two moving bristle fields in a brush section to provide an increased moving bristle area and improved cleaning, polishing, whitening, massaging and stimulating of teeth and gums. The first bristle field includes a plurality of bristles attached to a first bristle carrier that is powered and driven in a first motion pattern by a first drive member. The second bristle field includes a plurality of brush elements attached to the brush section. An extension member having an end attached to the first bristle carrier extends outwardly therefrom and at least partially extends into the second bristle field. In this powered toothbrush, the extension moves upon movement of the first bristle carrier to move the second bristle field in a second motion pattern.

The bristles in both the first and second bristle field may be made of either an elastomeric or non-elastomeric materials or any combination thereof to provide sufficient cleaning, polishing, whitening and stimulation to the teeth and gums.

Other features and advantages of the present invention will be apparent from the foregoing detailed description when read in conjunction with the accompanying drawings.

BRIEF DESCRIPTION OF THE DRAWING FIGURES

The foregoing and other features of the present invention will be more readily apparent from the following detailed description and drawings of illustrative embodiments of the invention in which.

DETAILED DESCRIPTION OF CERTAIN PREFERRED EMBODIMENTS OF THE PRESENT INVENTION

Figure 1A:
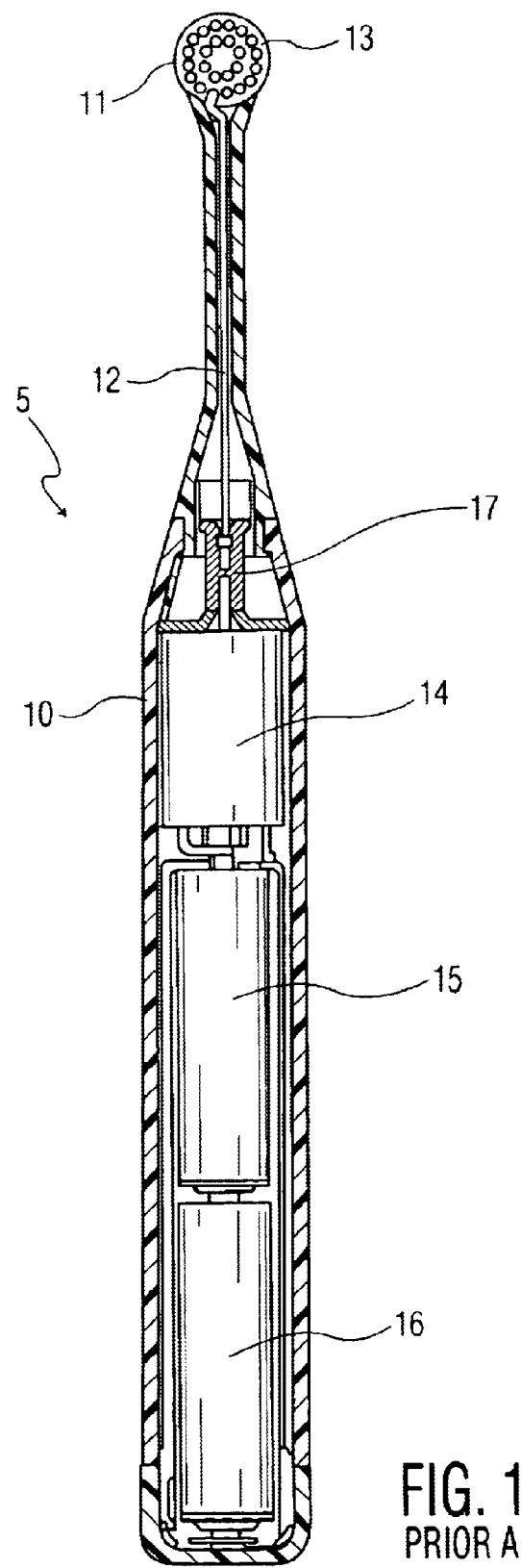
FIG. 1A is a front cross-sectional view of prior art powered toothbrush including a head.

Referring to FIGS. 2–12, a toothbrush 100 includes a handle 102 at a proximal end thereof that defines an interior compartment (not shown) for housing various components and a brush section 104 having a neck 106 and a head 120 at a distal end of the toothbrush 100. The neck 106 defines an interior compartment (not shown) for housing various working components of the toothbrush 100. The head 120 is preferably generally aligned with the longitudinal axis of the toothbrush 100.

In certain embodiments of the present invention, the brush section 104 is integrally formed with the handle 102. In other embodiments, the brush section 104 may be detachably connected to the handle 102 at a location along the toothbrush. Those skilled in the art will appreciate the various manners in which this may be accomplished, e.g., friction fit, threaded connection, interlocking or bayonet fitting, etc. Detachability of the brush section 104 may enable desirable features of the toothbrush 100, for example, cleaning, servicing, and/or replacement of either the handle 102 or the brush section 104. It will be appreciated that in such embodiments the head 120 may thus be a refill head type.

It will further be appreciated that the illustrated shapes of the handle 102 and brush portion 104 are merely exemplary in nature and the handle 102 and/or neck 106 can be formed to have a variety of shapes. The shapes of the handle 102 and the neck 106 may be of an aesthetic and/or ergonomic design such that the toothbrush 100 may be easily and comfortably gripped and manipulated by the user. By way of example, the handle 102 may include slightly recessed finger sections 118a, 118b that are formed on opposite sides of the handle 102. One recessed finger section 118a may be designed to generally accommodate a thumb of one hand and other recessed finger sections 118b may be designed to generally accommodate one or more other fingers of the same hand, thereby assisting the user in obtaining a secure grip of the toothbrush 100 in the user's hand to enhance proper placement. One or more of the recessed finger sections 118 may include ribs or other types of roughened surfaces to further assist gripping. Such surfaces, e.g., rubber, are generally known in the art and have acceptable frictional characteristics.

The toothbrush 100 according to the various embodiments disclosed herein can be made from any number of materials that are suitable for use in oral care products, such as toothbrushes, etc. For example, many of the components that are included in the toothbrush 100 are formed from plastic materials. Accordingly, the handle 102, brush section 104 and/or head 120 may be molded from polyolefins such as polypropylenes and polyethylenes, polyamids such as nylons, and polyesters such as polyethylene terephthalate. Other suitable materials include polymethylmethacrylate, styrene acroylonitrate and cellulose esters, for example cellulose propionate, and other materials known in the art.

The head 120 of the toothbrush 100 includes a head base 160 that at least partially defines an inner compartment (not shown) of the head 120. The head base 160 may be configured so that the distal end of the toothbrush 100 has a generally rounded shape for the comfort of the user during brushing.

The head 120 also includes a first movable bristle carrier 180, which in the illustrated embodiment is located towards the distal end of the head 120. However, the first bristle carrier 180 may be located at any location on the head 120.

Figure 1B:
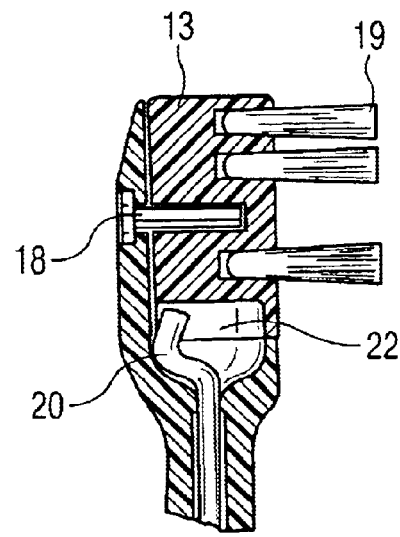
FIG. 1B is a partial cross-sectional side view of the toothbrush head of FIG. 1A.
Figure 1C:
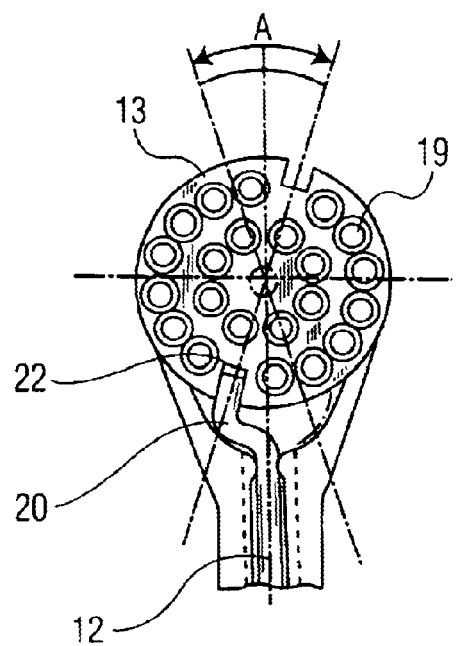
FIG. 1C is a partial cross-sectional front view of the toothbrush head of FIG. 1A.
Figure 2:
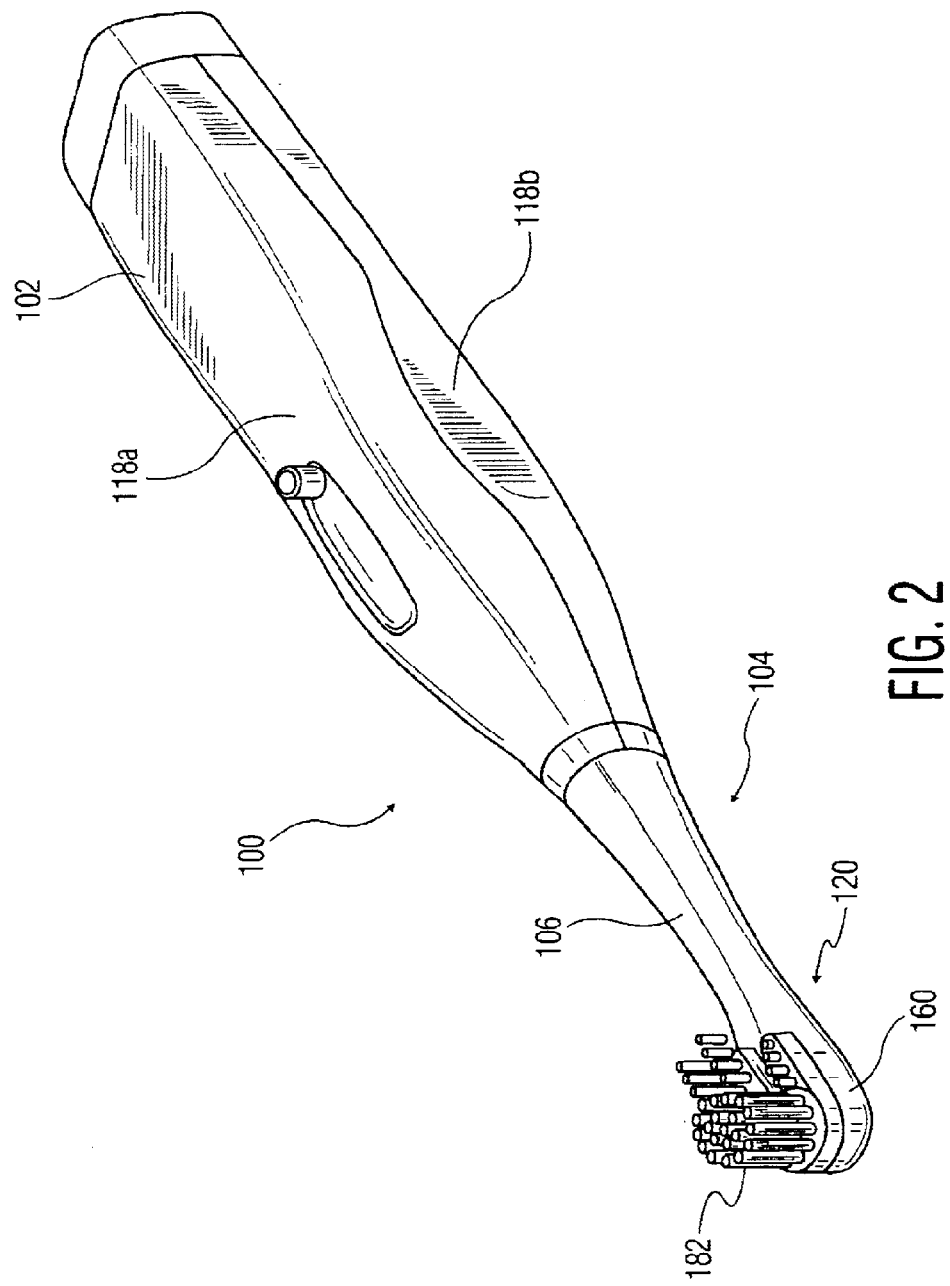
FIG. 2 is a perspective view of a preferred embodiment of a powered toothbrush in accordance with the teachings of the present invention.

The first bristle carrier 180 may be configured such that it may be at least partially rotatable around an axis. In such embodiments the first bristle carrier 180 may move in an oscillating or vibrating rotational manner. For example, the first bristle carrier may have an identical or similar construction to the bristle holder 12 illustrated in FIGS. 1A–1C. In such embodiments, the first movable bristle carrier 180 may be a circular disk. A circular shape requires a minimal amount of clearance to accommodate rotational or oscillating movement. However, it will be appreciated that the first movable bristle carrier 180 is not limited to having a disk shape and can have any number of different shapes, e.g., oval, regular or irregular shapes, so long as it may oscillate in a rotational or oscillating manner.

The first bristle carrier 180 includes a first bristle field 182 comprising a first plurality of bristles 185 coupled to and extending generally outwardly from the first bristle carrier 180. As is shown in the preferred embodiment, the plurality of bristles 185 of the first bristle field 182 includes two bristle arrays 185a and 185b formed in generally concentric circular paths. As used herein, the term "bristle" or "bristles" includes any type of structure that is suitable for providing oral health benefits (e.g., tooth cleaning, tooth polishing, tooth whitening, etc.) during contact with surfaces of the teeth. The bristles 185 may have a degree of flexibility so as to bend and flex during brushing so that they tend to conform to the surface and contours of the teeth and gums, thereby increasing bristle contact with the teeth and gum for improved effectiveness.

The bristles 185 of the first bristle field 182 may be composed of various materials. For example, they may be composed of non-elastomeric materials or elastomeric materials. As used herein, the term "elastomeric" means that the material undergoes a relatively greater elongation under tensile force or stress, wherein the term "non-elastomeric" means that the material has a relatively lesser elongation under tensile force or stress. Examples of suitable generally non-elastomeric materials include, but are not limited to, polyamides such as nylon or polyesters such as polybutylene terephthalate. Examples of suitable generally elastomeric materials include, but are not limited to, rubbers (synthetic or natural) and block copolymers such as, e.g., styrenes (for example styrene ethylene butadiene styrene, or styrene butadiene styrene), polyolefins (for example polypropylene/ethylene propylene diamine modified systems (i.e. synthetic rubber), polyamides (for example polyamide (2 or polyamide 6), polyesters (for example polyester ester or polyether ester), polyurethanes (for example polyesterurethane, polyetherurethane or polyesteretherurethane). For either elastomeric or non-elastomeric bristles, it is generally desirable that they are formed in such a manner so that they generally return to their original shape and size after brushing forces are removed, i.e., that they are non-plastic.

Non-elastomeric bristles may be coupled to the head 120, e.g., the first bristle carrier 180, in the form of tufts. The bristles and/or tufts may be coupled by various means, such as stapling, or may be molded (IMT) onto the head 120 during fabrication, or by other known means. Elastomeric bristles may be fabricated by known processes, such as molding, and coupled to the head by known means.

Although, as shown in the figures, the bristles 185 have particular sizes, shapes, amounts, lengths, configurations, materials and combinations thereof, it should be appreciated that the bristles 185 shown in the figures are merely illustrative and that they may be of any size, shape, amount, length, configuration, material and combination thereof suitable for oral hygiene. Such alternatives may be utilized to achieve specific results, such as, e.g., to create a particular movement from the moving tuft heads to deliver additional oral health benefits like enhanced cleaning, tooth polishing and/or tooth whitening. By way of example, the bristles may be of different (non-uniform) lengths to form a particular surface envelope shape for improved effectiveness. Further alternatives utilized may also be to accommodate differences between toothbrush users, including desired results, mouth size, teeth shape and contour, tooth and gum sensitivity, eating and other oral habits (e.g., smoking), and personal preferences.

Figure 5:
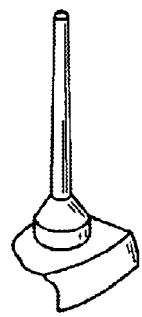
FIG. 5 is a perspective view of a preferred embodiment of an elastomeric bristle adapted for use in the toothbrush head of FIGS. 3–4.
Figure 6:
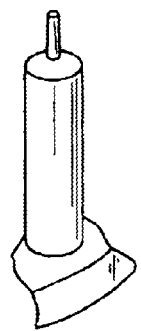
FIG. 6 is a perspective view of another preferred embodiment of an elastomeric bristle adapted for use in the toothbrush head of FIGS. 3–4.
Figure 7:
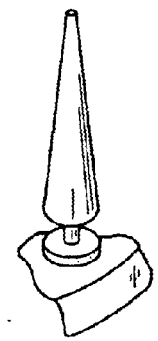
FIG. 7 is a perspective view of another preferred embodiment of an elastomeric bristle adapted for use in the toothbrush head of FIGS. 3–4.
Figure 8:
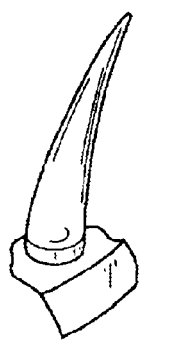
FIG. 8 is a perspective view of a still further preferred embodiment of an elastomeric bristle adapted for use in the toothbrush head of FIGS. 3–4.
Figure 9:
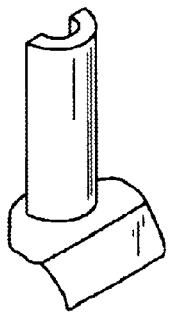
FIG. 9 is a perspective view of yet another preferred embodiment of an elastomeric bristle adapted for use in the toothbrush head of FIGS. 3–4.

One characteristic of certain elastomeric bristles is the capability of fabricating the elastomeric bristles into various configurations. FIGS. 5–9 illustrate various embodiments of elastomeric bristles. FIG. 5 shows an elastomeric bristle in the form of a thin spike; FIG. 6 shows an elastomeric bristle in the form of a barrel spike; FIG. 7 shows an elastomeric bristle in the form of a squeegee point; FIG. 8 shows an elastomeric bristle in the form of an angled point; and FIG. 9 shows an elastomeric bristle in the form of a section of an elastomeric wall. An elastomeric wall as in FIG. 9 may have a linear, planar shape; a zigzag shape; a serpentine shape, etc. All of the above elastomeric bristles can have smooth textures or can have rough surfaces. In addition, the wall sections of the elastomeric bristles may be vertically straight, taper inward toward one end or expand toward one end. The tops of the elastomeric bristles may have a planar surface or can have a protrusion (i.e., hump) or the like formed thereat. While the above describes various configurations of elastomeric bristles, those skilled in the art will recognize that virtually any configuration may be utilized.

Figure 10:
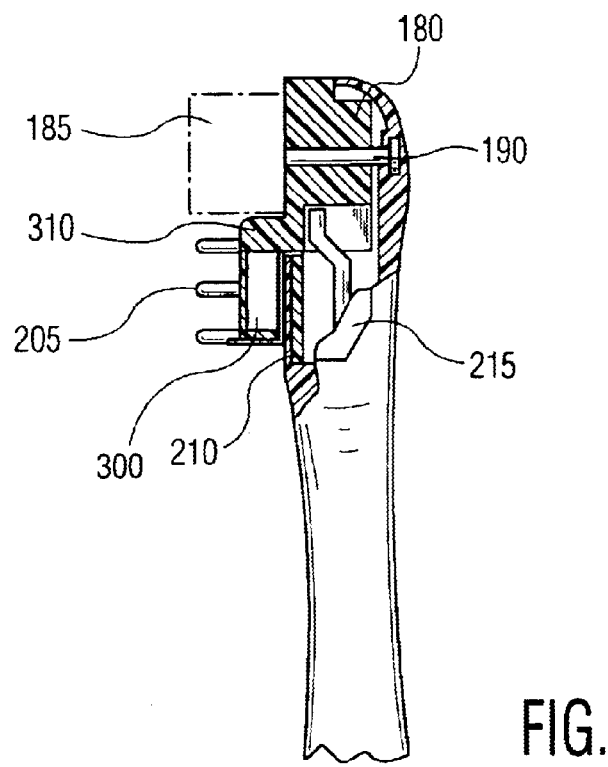
FIG. 10 is a partial side sectional view of the toothbrush head of FIG. 3 taken along line 10—10 of FIG. 3.
Figure 11:
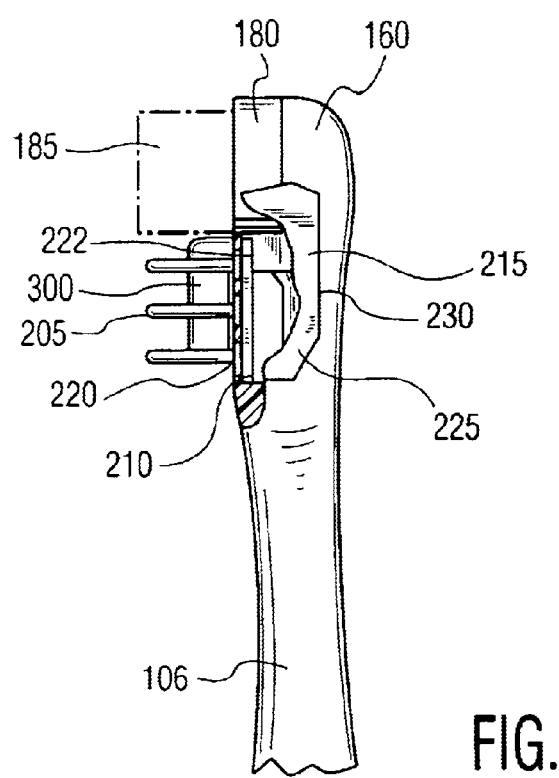
FIG. 11 is a partial side sectional view of the toothbrush head of FIG. 3.
Figure 14:
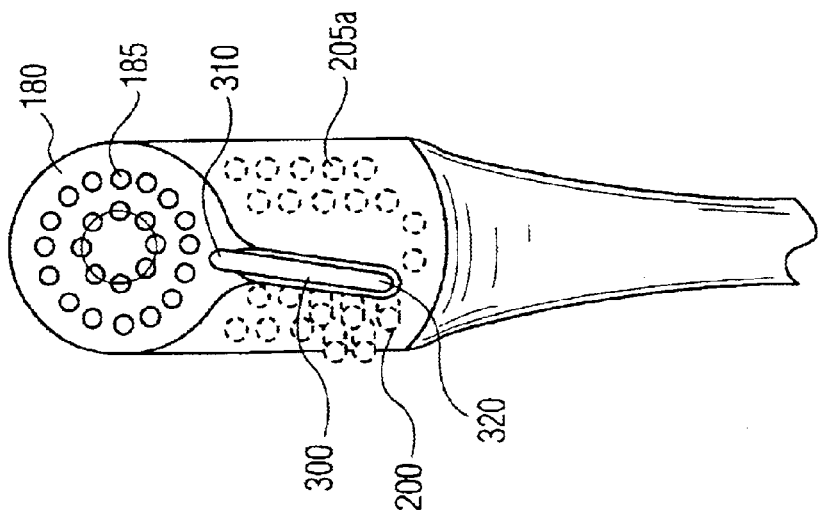
FIG. 14 is a front elevational view of the toothbrush head of FIG. 13 during an operational mode thereof.
Figure 12:
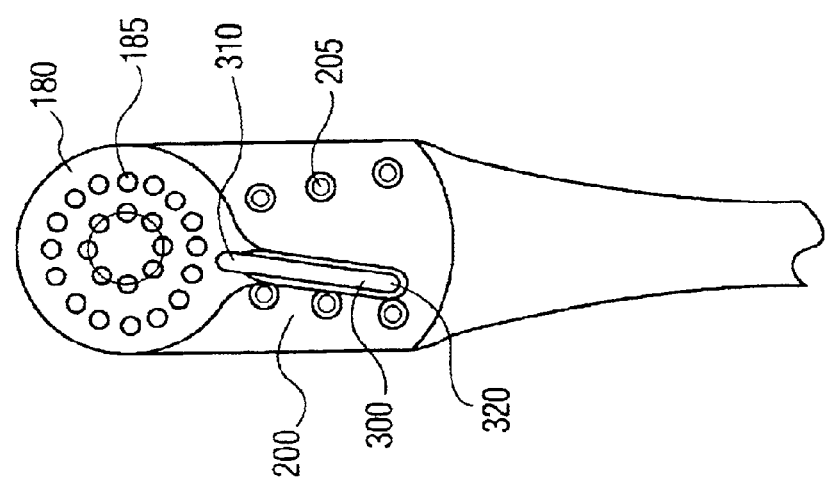
FIG. 12 is front elevational view of the toothbrush head of FIGS. 3 and 11 during an operational mode.

As seen in FIGS. 10, 12 and 14, the first bristle carrier 180 may be adapted to be pivotally rotatable around an axis generally perpendicular to the head base 160, thereby effectuating a rotational or circular movement of the bristles. In various embodiments, the first bristle carrier 180 may rotate around a post 190 (see FIG. 10), although any suitable configuration that permits such movement may be used. The movement of the first bristle carrier 180 may be oscillating or vibrational such that the first bristle carrier 180 first pivots about the post 190 in one direction through a range of motion and then pivots about the post 190 in the opposite direction through a range of motion, e.g., counterclockwise, then clockwise, and then repeats the sequence.

An oscillating motion has advantages over known toothbrushes that continuously rotate in one direction in that the variation of direction and speed of the bristles during oscillation provides improved cleaning and stimulation. Although in an oscillating system of the invention the bristles may rotate through any range of motion, it has been found that ranges of motion from about 10° to about 120° are effective in cleaning, whitening and stimulating. It has further been found that ranges of motion from about 10° to about 30° are also effective, and further provide the benefits of reduced cost and complexity of the toothbrush drive mechanism.

The drive mechanism for the powered toothbrush 100 may be any type of drive, e.g., a rotating drive, an oscillating drive, an eccentric drive, an unbalanced generated drive, a drive having one more gearing mechanisms, or any other type of drive mechanism that is capable of performing the intended function. The drive mechanism may be realized in the form of an electric motor or other type of motor and the movement generated by the drive may be imparted to one or more sections of the head 120 or to other elements that may be present at the brush section 104. The movement may be imparted directly or indirectly. Those skilled in the art will appreciate various suitable drive mechanisms.

One suitable mechanism is similar to the types described in U.S. Pat. No. 5,625,916 to McDougall, which has been previously incorporated herein, and in FIGS. 1A–1C. As described above, such a mechanism may be used to impart motion to the first bristle carrier. Those skilled in the art, however, will appreciate that variations in the details of the illustrated mechanism may be implemented as long as it performs its intended function.

The brush section 104 further includes a second bristle field 200 comprising a second plurality of bristles 205. The second plurality of bristles 205 may be of any size, shape, amount, length, configuration, material and combinations thereof, as described heretofore regarding the first plurality of bristles 185. Accordingly, the written description above regarding the first plurality of bristles 185 is equally applicable to the second plurality of bristles 205, and is incorporated therefrom as if set out once more. It thus should be understood that the second bristle field 200 as contemplated by the invention is not limited to the embodiments illustrated in the Figures.

By way of example, the second bristle field 200 illustrated in FIGS. 3, 4, 10, 11 and 12 includes elastomeric bristles 205. In the embodiment shown in FIG. 3, the elastomeric bristles 205 are symmetrically formed on sides of an extension 300 to be discussed in further detail below. As shown, the bristles 205a, 205b and 205c are arranged in a downwardly inclined manner toward the side edges of the bristle base 210. The bristle 205d is arranged inwardly from the bristle 205c.

The bristles 205 may be integrally formed with, e.g., molded, and extend from a bristle base 210. The bristles 205 and bristle base 210 may be attached to the brush section 104 by a bristle cap 215. In the illustrated embodiments, the bristle cap 215 locates the bristle base 210 between the bristle cap 215 and the brush section 104 and has openings 220 through which the bristles 205 extend. The bristle cap 215 may engage with the brush section 104 by any manner suitable to attach the bristle base 210 thereto, including but not limited to, snap fit, fastener(s), adhesive, etc. The bristle cap 215 may be adapted so that it does not disengage from the brush section 104 during use. The brush section 104 may include an indent 222 to receive the bristle base 210 and bristle cap 215 so that the exterior surface 225 of the bristle cap 215 is substantially flush with the surrounding surface 230 of the brush section 104.

Figure 13:
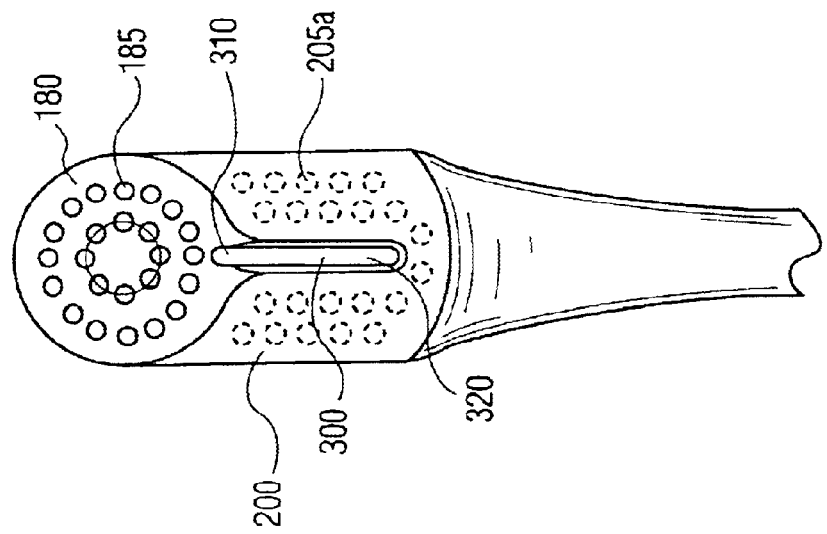
FIG. 13 is a front elevational view of a further preferred embodiment of a toothbrush head in accordance with the teachings of the present invention.

In other embodiments, such as illustrated in FIGS. 13 and 14, the second bristle field comprises non-elastomeric bristles 205'. The non-elastomeric bristles 205' may be attached to the brush section 104 in any suitable manner, such as described heretofore, e.g., stapled, IMT, etc. Those skilled in the art will appreciate other bristle configurations for use with the invention.

The brush section 104 further includes an extension 300. In one preferred embodiment, the extension 300 has a fixed end 310 attached to the first bristle carrier 180 and a free end 320 generally extending from the first bristle carrier 180 and at least partially into the second bristle field 200 such that the extension 300 is generally proximate to one or more bristles 205 or 205'. In another preferred embodiment, the extension 300 can be integrally formed with the disk-shaped member of the first bristle carrier 180 and extends from a peripheral edge of the disk-shaped member. The extension 300 may be configured so that it does not extend beyond the second bristle field 200, e.g., in the lateral and/or vertical direction, in order to minimize contact between the extension 300 and teeth and gums during operation. The extension 300 may be integrally formed with the first bristle carrier 180, e.g., molded, or it may be attached to the first bristle carrier 180 in any suitable manner such that it does not detach therefrom during operation of the toothbrush 100.

As illustrated in FIGS. 12 and 14, during oscillation of the first bristle carrier 180, the extension 300 also oscillates. Thus, during an oscillation of the first bristle carrier 180, the first bristle carrier 180 first moves in a first direction relative to the toothbrush head 120 and the extension 300 correspondingly moves in that first direction. This causes the extension 300 to contact one or more bristles 205 or 205' in the second bristle field 200 and deflect or move them. The first bristle carrier 180 then moves in a second direction, whereby the extension 300 ceases to contact the bristles 205 or 205' and the bristles 205 or 205' return to a substantially non-deflected position. During a subsequent oscillation of the first bristle carrier 180, the above-described movement of the bristles is repeated. Hence, the bristles 205 or 205' move in an oscillating manner at a frequency approximately equal to the oscillation frequency of the first bristle carrier 180. The motion of the bristles 205 or 205' provides additional area and number of moving bristles on the toothbrush, increasing its effectiveness.

Due to the manner of contact between the extension 300 and the bristles 205 or 205', the motion of individual bristles 205 or 205' is generally linear in nature. Thus, the toothbrush of the present invention provides at least two distinct modes of bristle motion-the generally rotational motion of the first bristle field and the generally linear motion of the second bristle field. These different motions, and the combination thereof, enhance the effectiveness of the toothbrush, e.g., cleaning, polishing, stimulating, etc.

In addition, the extension 300 can have a height that is less than the height of each bristle element 205 or 205' that defines the second bristle field 200. However, the extension 300 can be any height so that it impinges upon the bristle elements 205 or 205' and imparts sufficient generally linear motion thereto. Moreover, the extension can be of any material which will impart sufficient linear motion to the bristles of the second bristle field. Therefore, the extension 300 can be formed of either a rigid material or an elastomeric material.

It will also be appreciated that in another embodiment, the extension 300 can have two free ends and instead of being driven by the first bristle carrier 180, the extension 300 is driven by a drive mechanism that can be a part of the same drive mechanism that drives the first bristle carrier 180 or it can be a different drive mechanism. For example, the extension 300 can include a shaft (not shown) that extends into the inner compartment of the brush section 104. The shaft is either coupled to or in selective contact with the drive mechanism to cause the extension 300 to move in such away that the extension 300 contacts one or more bristles 205 or 205'.

Figure 3:
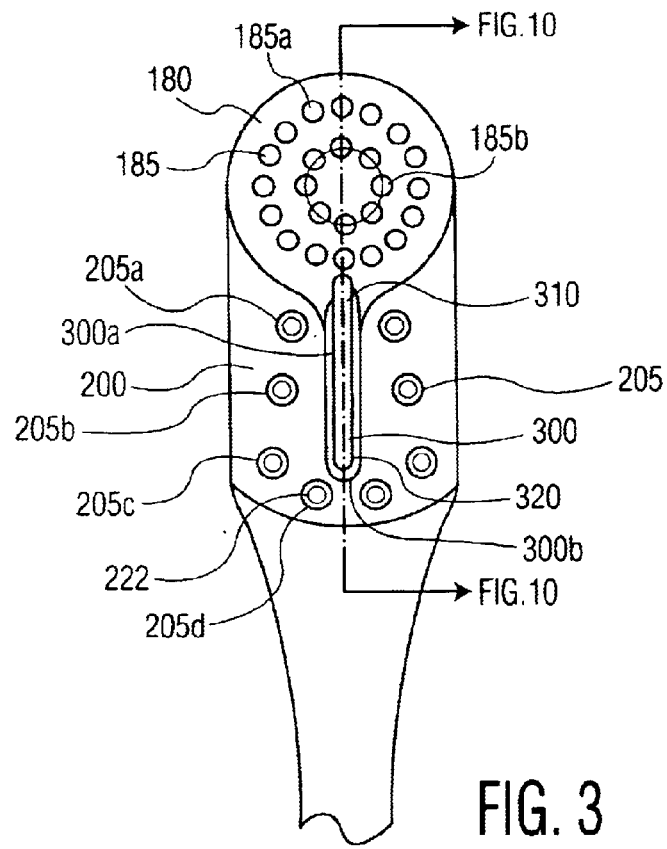
FIG. 3 is a front elevational view of a preferred embodiment of a toothbrush head utilized in the powered toothbrush of FIG. 2.
Figure 4:
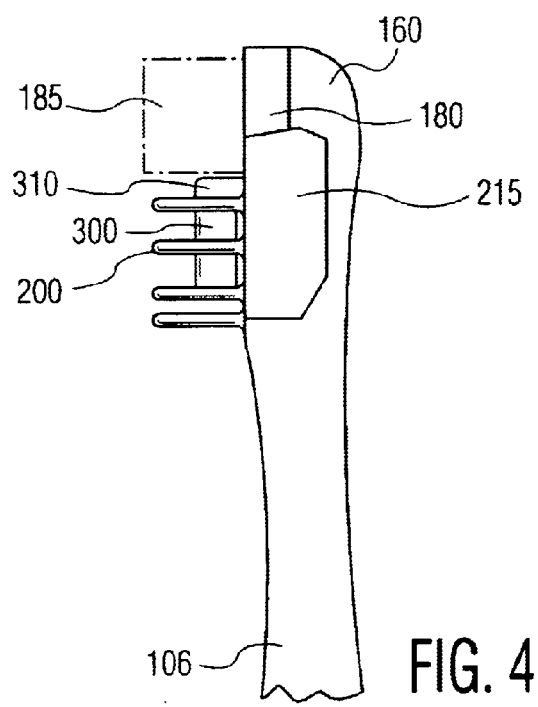
FIG. 4 is a side elevational view of a toothbrush head of FIG. 3.

In addition, as shown in FIG. 3, at least some of the bristles of the second bristle field, such as bristles 205a, 205b and 205c extend in a row pattern longitudinally along a first side face 300a of the extension 300, and at least some of the bristles, such as 205c and 205d, extend longitudinally in a row pattern along a second side face 300b of the extension. FIG. 3 further illustrates that the bristles 205a, 205b, 205c and 205d of the second bristle field 205 can surround the free end of the extension 300.

A powered toothbrush made in accordance with the present invention provides a number of advantages over known powered toothbrushes that are presently available. For example, in embodiments having a first bristle field that oscillates back and forth, or moves otherwise, the oscillating bristles (i.e., clastomeric and/or non-elastomeric) contact the surfaces of the teeth and the surrounding areas to deliver enhanced cleaning, stimulation, and tooth polishing and/or whitening. Further, embodiments having a second bristle field may provide additional bristles that may be disposed in various patterns and combinations different from those of the first bristle field. These bristles may move in a different manner than those of the first bristle field, which along with the additional. number and area of moving bristles, provide increased contact with teeth and gingival tissues for enhanced cleaning and stimulating over known powered toothbrushes.

Although powered toothbrushes of the present invention have been described in terms of the presently preferred embodiments, it is to be understood that such disclosure is not to be interpreted as limiting. It will be understood that various omissions, substitutions, and changes in the form and details of the devices illustrated, and in their operation, may be made by those skilled in the art without departing from the spirit and scope of the invention. For example, it is expressly intended that all combinations of those elements and/or steps which perform substantially the same function, in substantially the same way, to achieve the same results are within the scope of the invention. Substitutions of elements from one described embodiment to another are also fully intended and contemplated. It is also to be understood that the drawings are not necessarily drawn to scale, but that they are merely conceptual in nature. Accordingly, it is intended that the appended claims be interpreted as covering all alterations and modifications as fall within the true spirit and scope of the invention.

What is claimed is:

1. A toothbrush comprising: a handle portion having a neck formed at one end; and a head coupled to the neck, the head including a first bristle carrier coupled to the head and having a first bristle field extending outwardly therefrom, said first bristle carrier being operatively connected to a drive mechanism for moving said first bristle field in a first path of motion; a second bristle field extending from a base support of said head; and an extension having an end attached to said first bristle carrier and extending outwardly therefrom, not in contact with said base and at least partially into said second bristle field whereby said extension moves upon movement of said first bristle carrier to move said second bristle field in a second path of motion.

2. The toothbrush of claim 1, wherein the first bristle carrier oscillates in a rotational direction to cause the first path of motion of the first bristle field to be in a generally rotational direction, and the oscillation of the first bristle carrier causes the extension to contact and move the second bristle field in the second path of motion which is generally linear.

3. A toothbrush comprising:
 a handle portion having a neck formed at one end; and
 a head coupled to the neck, the head including:
  a first bristle carrier coupled to the head and operatively connected to a first drive mechanism, the first bristle carrier having a first bristle field formed thereon; and
  an extension attached to said first bristle carrier and extending outwardly therefrom towards the handle portion and at least partially into a second bristle field such that movement of the first bristle carrier in a first path of motion causes the extension to contact and move brush elements that are contained within the second bristle field in a second path of motion.

4. The toothbrush of claim 3, wherein the first bristle carrier is moved in a direction which is about an axis generally perpendicular to an outer surface of the head.

5. The toothbrush of claim 3, wherein the first bristle carrier oscillates in a back and forth manner.

6. The toothbrush of claim 3, wherein the first bristle carrier is oscillated in a rotational direction.

7. The toothbrush of claim 3, wherein the extension is integrally formed with the first bristle carrier so that the extension moves in the same direction as the first bristle carrier.

8. The toothbrush of claim 3, wherein the extension comprises an elongated member that is disposed parallel to a longitudinal axis of the head.

9. The toothbrush of claim 8, wherein a section of the extension is disposed above an upper surface of the head.

10. The toothbrush of claim 3, wherein the extension has a first end that is attached to the first bristle carrier and an opposing free second end that extends at least partially into the second bristle field.

11. The toothbrush of claim 10, wherein the first end is disposed outside of the first bristle field.

12. The toothbrush of claim 3, wherein the second bristle field includes a bristle base and a plurality of bristles that extend therefrom, the bristle base being coupled to the head.

13. The toothbrush of claim 12, wherein the bristle base is coupled to the head by a bristle cap which is securely coupled to the head, the bristle cap wrapping around opposing sidewalls of the head.

14. The toothbrush of claim 12, wherein the plurality of bristles include at least some elastomeric bristles.

15. The toothbrush of claim 3, wherein the second bristle field includes a plurality of bristles, the extension being disposed between a first group of bristles and a second group of bristles.

16. The toothbrush of claim 3, wherein a free end of the extension is contained within the second bristle field.

17. The toothbrush of claim 3, wherein the second path of motion is characterized by a plurality of bristles moving linearly upon the extension striking the plurality of bristles as the first bristle carrier moves in the first path of motion.

18. The toothbrush of claim 3, wherein the extension has a height that is less than a height of each bristle element that defines the second bristle field.

19. The toothbrush of claim 3, wherein the first bristle carrier comprises a disk-shaped member with the extension being integrally formed therewith and extending from a peripheral edge of the disk-shaped member.

20. The toothbrush of claim 3, wherein the extension has a first end that is attached to the first bristle carrier and an opposing free second end that extends at least partially into the second bristle field.

21. The toothbrush of claim 3, wherein the second bristle field includes a plurality of bristle rows, at least some of the bristle rows extending longitudinally along a first side face of the extension and at least some of the rows extending longitudinally along a second side face of the extension.

22. The toothbrush of claim 21, wherein a plurality of bristle elements of the second bristle field surround a free end of the extension.

23. The toothbrush of claim 3, wherein the first drive member comprises a drive shaft operatively connected to said first bristle carrier.

24. The toothbrush of claim 3, wherein the second bristle field is located closer to the handle portion than the first bristle field.

25. The toothbrush of claim 3, wherein the second bristle field has bristles of varying height.

26. The toothbrush of claim 3, wherein the second bristle field is formed of at least two different types of bristles.

27. The toothbrush of claim 3, wherein the extension is formed of a rigid material.

28. The toothbrush of claim 3, wherein the extension is formed of an elastomeric material.

* * * * *

UNITED STATES PATENT AND TRADEMARK OFFICE
CERTIFICATE OF CORRECTION

PATENT NO. : 6,813,793 B2
DATED : November 9, 2004
INVENTOR(S) : Eyal Eliav

It is certified that error appears in the above-identified patent and that said Letters Patent is hereby corrected as shown below:

Column 10,
Line 45, delete the first appearance of the word "first".

Signed and Sealed this

Sixteenth Day of August, 2005

JON W. DUDAS
*Director of the United States Patent and Trademark Office*